(12) United States Patent
Hargreaves et al.

(10) Patent No.: US 11,313,933 B2
(45) Date of Patent: Apr. 26, 2022

(54) DIFFUSION-WEIGHTED MRI WITH MAGNITUDE-BASED LOCALLY LOW-RANK REGULARIZATION

(71) Applicant: The Board of Trustees of the Leland Stanford Junior University, Stanford, CA (US)

(72) Inventors: Brian A. Hargreaves, Menlo Park, CA (US); Yuxin Hu, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 196 days.

(21) Appl. No.: 16/824,582

(22) Filed: Mar. 19, 2020

(65) Prior Publication Data

US 2020/0300956 A1 Sep. 24, 2020

Related U.S. Application Data

(60) Provisional application No. 62/820,922, filed on Mar. 20, 2019.

(51) Int. Cl.
*G01R 33/563* (2006.01)
*A61B 5/055* (2006.01)
(Continued)

(52) U.S. Cl.
CPC ...... *G01R 33/56341* (2013.01); *A61B 5/0042* (2013.01); *A61B 5/055* (2013.01);
(Continued)

(58) Field of Classification Search
CPC .......... G01R 33/56341; G01R 33/5608; A61B 5/0042; A61B 5/0055; G06T 5/50; G06T 7/0012
See application file for complete search history.

(56) References Cited

U.S. PATENT DOCUMENTS

| 11,009,577 | B2 * | 5/2021 | McKay | ............ | G01R 33/56554 |
| 2009/0284257 | A1 * | 11/2009 | Bammer | ............ | G01R 33/56509 |
| | | | | | 324/307 |

(Continued)

OTHER PUBLICATIONS

Hu Y, Tian Q, Yang G, McNab J, Daniel B, Hargreaves B, "A nonlinear model for DTI reconstruction with locally low-rank regularization," In Proceedings of the Joint Annual Meeting ISMRM-ESMRMB. Montreal, Canada; May 2019, p. 0234.

(Continued)

*Primary Examiner* — Dixomara Vargas
(74) *Attorney, Agent, or Firm* — Lumen Patent Firm

(57) ABSTRACT

A diffusion-weighted magnetic resonance imaging (MRI) method acquires MRI scan data from a multi-direction, multi-shot, diffusion-weighted MRI scan, and jointly reconstructs from the MRI scan data 1) magnitude images for multiple diffusion-encoding directions and 2) phase images for multiple shots and multiple diffusion-encoding directions using an iterative reconstruction method. Each iteration of the iterative reconstruction method comprises a gradient calculation, a phase update to update the phase images, and a magnitude update to update the magnitude images. Each iteration minimizes a cost function comprising a locally low-rank (LLR) regularization constraint on the magnitude images from the multiple diffusion-encoding directions.

5 Claims, 11 Drawing Sheets

(51) Int. Cl.
*A61B 5/00* (2006.01)
*G01R 33/56* (2006.01)
*G06T 5/50* (2006.01)
*G06T 7/00* (2017.01)

(52) U.S. Cl.
CPC ............ *G01R 33/5608* (2013.01); *G06T 5/50* (2013.01); *G06T 7/0012* (2013.01); *G06T 2207/10092* (2013.01); *G06T 2207/20021* (2013.01); *G06T 2207/30016* (2013.01)

(56) References Cited

U.S. PATENT DOCUMENTS

| | | | |
|---|---|---|---|
| 2013/0182932 A1* | 7/2013 | Chen | G06T 11/008 382/131 |
| 2014/0376794 A1* | 12/2014 | Dumoulin | G01R 33/5611 382/131 |
| 2015/0279065 A1* | 10/2015 | Li | G01R 33/5611 382/131 |
| 2015/0346303 A1* | 12/2015 | Hu | G06T 11/006 600/420 |
| 2017/0108570 A1* | 4/2017 | Eichner | G01R 33/5608 |
| 2017/0178318 A1* | 6/2017 | Wang | G06T 11/008 |
| 2018/0210054 A1* | 7/2018 | Hu | G01R 33/5601 |
| 2019/0004132 A1* | 1/2019 | Tan | G01R 33/5611 |
| 2019/0212406 A1* | 7/2019 | Meineke | G01R 33/56 |
| 2019/0302211 A1* | 10/2019 | Cai | G06T 11/008 |
| 2020/0034998 A1* | 1/2020 | Schlemper | G06F 17/142 |

OTHER PUBLICATIONS

Shi, Xinwei, et al. "Parallel imaging and compressed sensing combined framework for accelerating high-resolution diffusion tensor imaging using inter-image correlation." Magnetic resonance in medicine 73.5 (2015): 1775-1785.

Ma, Sen, et al. "Accelerated Cardiac Diffusion Tensor Imaging Using Joint Low-Rank and Sparsity Constraints." arXiv preprint arXiv:1801.03525 (2018).

Gao, Hao, et al. "PCLR: Phase-constrained low-rank model for compressive diffusion-weighted MRI." Magnetic resonance in medicine 72.5 (2014): 1330-1341.

Veraart, Jelle, et al. "Denoising of diffusion MRI using random matrix theory." NeuroImage 142 (2016): 394-406.

Hu, Yuxin, et al. "Motion-robust reconstruction of multishot diffusion-weighted images without phase estimation through locally low-rank regularization." Magnetic resonance in medicine (2018).

Ong, Frank, Joseph Y. Cheng, and Michael Lustig. "General phase regularized reconstruction using phase cycling." Magnetic resonance in medicine 80.1 (2018): 112-125.

Pruessmann, Klaas P., et al. "SENSE: sensitivity encoding for fast MRI." Magnetic resonance in medicine 42.5 (1999): 952-962.

Hu, Yuxin, et al. Multi-shot diffusion-weighted MRI reconstruction with magnitude-based spatial-angular locally low-rank regularization (SPA-LLR). Magnetic resonance in medicine 83.5 (2020): 1596-1607.

* cited by examiner

| Parameters | Ex0 (to validate the method) | Ex1 (parameter selection) | Ex2 4-shot vs single-shot (R = 3) | | Ex3 (different resolutions) | Ex4 (more directions) | Ex5 (high b-value) |
|---|---|---|---|---|---|---|---|
| TR/TE (ms) | 3266/70 | 3375/50 | 2278/51 | 2478/64 | 2627/53, 2759/54, 2993/57 | 2853/53 | 2908/59 |
| Effective echo spacing (μs) | 334 | 264 | 245 | 324 | 264, 281, 310 | 264 | 245 |
| Scan time (min) | 6:45 | 08:09 | 22:58 | 24:58 | 13:21, 14:01, 15:13 | 28:46 | 14:47 |
| In-plane resolution (mm) | 2 | 0.9 | 1 | 1 | 0.9, 0.8, 0.7 | 0.9 | 1 |
| Slice thickness (mm) | 2 | 0.9 | 1 | 1 | 0.9, 0.8, 0.7 | 0.9 | 1 |
| FOV (cm) | 20 | 20 | 18.4 | | 20 | 20 | 20 |
| Number of slices | 12 | 14 | 10 | 4 | 11 | 12 | 10 |
| Partial Fourier factor | 1 | 0.61 | 0.67 | 0.75 | 0.64, 0.63, 0.61 | 0.64 | 0.66 |
| Number of directions | 60 | 30 | 150 | | 75 | 150 | 75 |
| Nex | 1 | 1 | 1 | | 1 | 1 | 1 |
| b-value | 2000 | 1000 | 1000 | | 1000 | 1000 | 2000 |
| Number of subjects | 1 | 1 | 1 | | 1 | 2 | 2 |

Fig. 11

DIFFUSION-WEIGHTED MRI WITH MAGNITUDE-BASED LOCALLY LOW-RANK REGULARIZATION

CROSS-REFERENCE TO RELATED APPLICATIONS

This application claims priority from U.S. Provisional Patent Application 62/820,922 filed Mar. 20, 2019, which is incorporated herein by reference.

STATEMENT REGARDING FEDERALLY SPONSORED RESEARCH OR DEVELOPMENT

This invention was made with Government support under contract EB015891 awarded by the National institutes of Health, and under contract EB009055 awarded by the National institutes of Health. The Government has certain rights in the invention.

FIELD OF THE INVENTION

The present invention relates generally to diagnostic imaging. More specifically, it relates to magnetic resonance imaging (MRI) reconstruction.

BACKGROUND OF THE INVENTION

Diffusion-weighted (DW) MRI non-invasively measures Brownian motion of water molecules along the direction of diffusion-encoding gradients. It has been widely used for clinical and neuroscientific applications. Typically, DW images are acquired using single-shot echo-planar imaging (EPI) to provide robustness against motion artifacts. However, in single-shot EPI, the spatial resolution and signal-to-noise ratio (SNR) are limited due to the long readout window, and distortion artifacts can be severe.

To enable high-resolution DW imaging (DWI) with reduced artifacts, numerous techniques such as simultaneous multi-slice imaging, multi-shot imaging, reduced field-of-view (FOV) imaging, image denoising, and some advanced image reconstruction methods have been proposed. Nonetheless, diffusion encoding leads to a motion-induced phase that varies between repetitions and may limit the application of many techniques to DWI.

To address this challenge, many navigator-less reconstruction methods have been proposed for multi-shot DWI. In MUSE, SENSE is first applied to each individual shot to estimate the motion-induced phase, which is then included into the forward model for a SENSE-like reconstruction. POCS-MUSE and POCS-ICE further improve this method by updating the phase estimation during each iteration. To bypass the phase estimation step, low-rank matrices in k-space and image space are constructed in MUSSELS and shot-LLR respectively, and matrix completion is performed to reconstruct multi-shot images.

Acquisition of DW images along multiple directions is needed for deriving microstructural metrics from diffusion models such as the diffusion tensor imaging (DTI), neurite orientation dispersion and density imaging (NODDI), and others. Some post-processing methods have been proposed to denoise each individual magnitude image based on various assumptions.

Efforts have been made to utilize the correlation between images of different encoding directions to enable higher reduction factors, increased SNR and reduced scan time. However, the random motion-induced phase after diffusion encoding makes it hard to utilize this correlation. Even worse, this phase variation exists between different shots for the same diffusion-encoding direction in multi-shot imaging. Typically, the motion-induced phase needs to be estimated and removed in reconstruction, which requires an accurate phase estimation.

Previous methods first estimate the low-resolution phase and then eliminate this phase when performing image reconstruction with constraints for correlations between different diffusion-encoding directions. Since the phase is fixed during later iterations, the residual phase variation due to inaccurate initial phase estimation decreases the angular correlation.

BRIEF SUMMARY OF THE INVENTION

The inventors have developed techniques to address the problem that motion-induced phase variations between different shots and different encoding directions in DWI make it hard to utilize their angular correlations and get high-resolution diffusion-weighted images.

To overcome this challenge, the invention provides a method for multi-shot DWI reconstruction, in which both the magnitude and phase images are iteratively and jointly estimated in all DW directions. This differs from existing methods as it separately reconstructs both magnitude and phase images rather than complex images. This property enables the direct application of constraints on the magnitude images without influence from phase variations.

In addition, a locally low-rank (LLR) regularization constraint applied to the multi-direction magnitude images is incorporated to exploit spatial and angular correlations between images from all different diffusion encoding directions.

This invention involves a non-convex, non-linear model with a data consistency term for multi-direction, multi-shot data and a locally low-rank regularization term to exploit angular correlations.

This method enables better depiction of small structures in the brain. At high spatial resolution, noise becomes a limitation, and these techniques can overcome this, enabling higher resolution images for analysis.

When compared with results from the MUSE reconstruction, a significantly reduced noise level can be visualized. In-vivo experiments demonstrate that using a non-linear model coupled with this spatial-angular LLR regularization (SPA-LLR), high-quality sub-millimeter resolution DWI can be achieved.

In summary, this invention is about a joint reconstruction method of multi-direction DWI, with simultaneous phase and magnitude estimation and spatial-angular LLR regularization on magnitude images. It simultaneously removes motion-induced phase artifacts and denoises images, improving the quality of high-resolution and high b-value DWI.

In one aspect, the invention provides a method for diffusion-weighted magnetic resonance imaging (MRI), the method comprising: performing by an MRI scanner a multi-direction, multi-shot, diffusion-weighted MRI scan to produce MRI scan data; jointly reconstructing from the MRI scan data magnitude images for multiple diffusion-encoding directions and phase images for multiple shots and multiple diffusion-encoding directions using an iterative reconstruction method. Each iteration of the iterative reconstruction method comprises a gradient calculation, a phase update to update the phase images, and a magnitude update to update the magnitude images. Each iteration minimizes a cost function comprising a locally low-rank (LLR) regularization constraint on the magnitude images from the multiple diffusion-encoding directions.

In some embodiments, the method further comprises decomposing images of the MRI scan data into magnitude images and phase images.

In some embodiments, the locally low-rank (LLR) regularization constraint on the magnitude images from the multiple diffusion-encoding directions includes a sum over local spatial image blocks.

In some embodiments, the locally low-rank (LLR) regularization constraint includes operators for local spatial image blocks, formed by concatenating vectors containing magnitude image data from multiple diffusion-encoding directions.

In some embodiments, the cost function comprises a data consistency term that sums over all diffusion-encoding directions and sums over all shots.

BRIEF DESCRIPTION OF THE SEVERAL VIEWS OF THE DRAWINGS

FIG. 11 is a table providing a summary of acquisition parameters of different experiments, according to embodiments of the present invention.

DETAILED DESCRIPTION OF THE INVENTION

In many applications, DW images along 30 or even more diffusion-encoding directions are acquired to fit diffusion models and obtain sufficient SNR. Redundancy exists between DW signals along different diffusion-encoding directions. To utilize this redundancy, embodiments of the present invention construct spatial-angular locally low-rank matrices from the magnitude images of all diffusion encoding directions and apply a rank penalty on the sum of ranks of these matrices.

Figure 1:
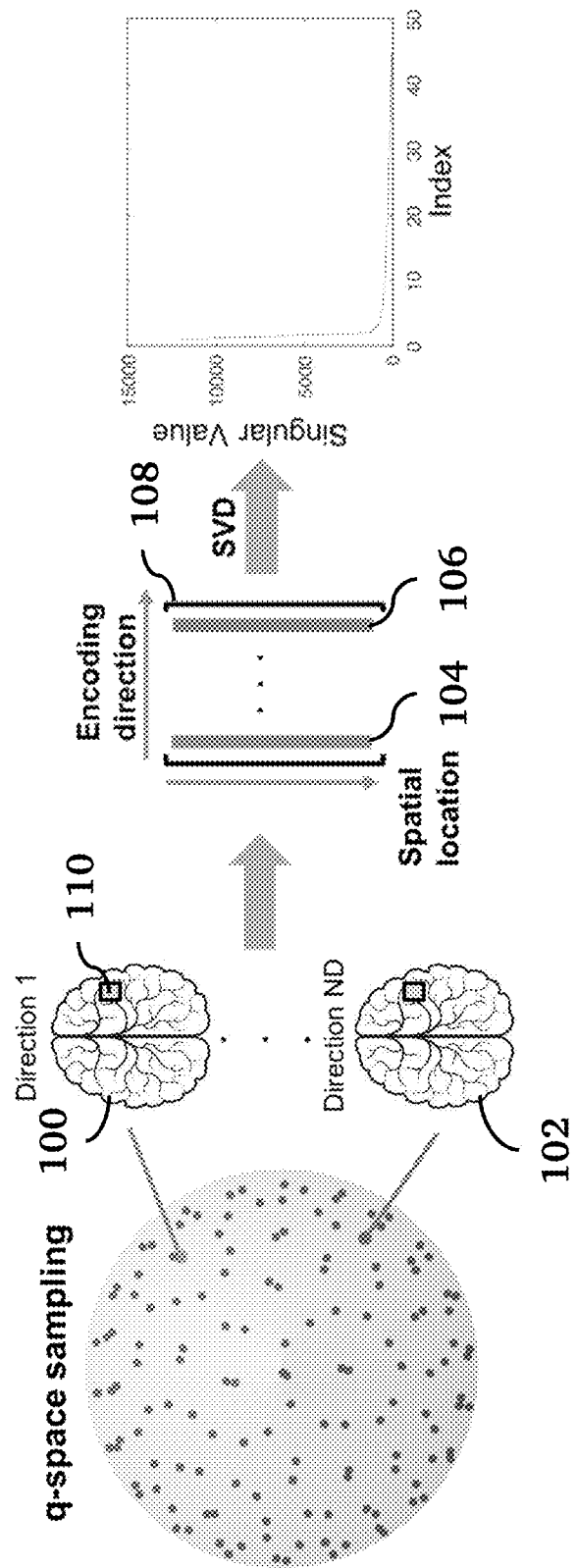
FIG. 1 is a schematic diagram illustrating the construction of a spatial-angular matrix from magnitude images of different diffusion-encoding directions, according to an embodiment of the invention.

As illustrated in FIG. 1, to construct a spatial-angular matrix, one small spatial block 110 is first chosen. The entire field of view (FOV) is covered by many local blocks 110. The magnitude images 100 to 102 along each of the ND diffusion-encoding (q-space) directions in this block are then reshaped into corresponding vectors 104 to 106. Finally, vectors 104 to 106 from all encoding directions are concatenated together to form the matrix 108. Each column of the matrix 108 represents one block of pixels from one diffusion-encoding direction. Singular value decomposition (SVD) is applied to the matrix. Most of the resulting eigenvalues of this matrix are close to 0, i.e., the rank of this matrix is low. This matrix is later used as a regularization term in reconstruction.

We now describe the details of the non-linear model used in formulating the reconstruction approach used in embodiment of the invention. The measured signal in DWI can be written in the following matrix form, $$y = EFSx + n, \quad (1)$$

where y denotes the acquired k-space signal, E, F and S represent the sampling operator, Fourier transform, and sensitivity encoding operator, respectively, x denotes the complex DW image to be estimated, and n denotes noise.

To utilize the angular correlation between magnitude images along different encoding directions, motion-induced phase variations need to be considered. The complex image can be written in terms of magnitude and phase explicitly, so the k-space signal for direction d, shot s, can be represented as $$y_{d,s} = E_{d,s} FS(m_d \cdot \exp(j\theta_{d,s})) + n, \quad (2)$$

where $m_d$ represents the magnitude image along the diffusion-encoding direction d, and $\exp(j\theta_{d,s})$ represents the phase image along the diffusion-encoding direction d for shot s, which may arise from $B_0$ inhomogeneity, bulk motion, eddy currents, or other sources.

Embodiments of the present invention use the following general model for joint reconstruction of multi-direction DWI:

$$\min_{m,\theta} \Sigma_d \Sigma_s \tfrac{1}{2} \| E_{d,s} FS(m_d \cdot \exp(j\theta_{d,s})) - y_{d,s} \|_2^2 + \lambda_1 g_m(m), \quad (3)$$

where the sum over d ranges from 1 to the number of diffusion encoding directions ND, the sum over s ranges from 1 to the number of shots NS, $m = [m_1, \ldots, m_{ND}]^T$ and $\theta$ is an ND×NS matrix with elements $\theta_{d,s}$.

The first term of Eq. 3 encourages consistency with the forward model based on Eq. 2, and the second term $g_m(m)$ is a regularization term to utilize the correlation between images from different diffusion-encoding directions.

Using LLR as the regularization term, the reconstruction can be formulated as the following problem, $$\min_{m,\theta} \Sigma_d \Sigma_s \tfrac{1}{2} \| E_{d,s} FS(m_d \cdot \exp(j\theta_{d,s})) - y_{d,s} \|_2^2 + \Sigma_{l \in \Omega} \| R_l m \|_*, \quad (4)$$

where $R_l$ is an operator that extracts and reshapes one local spatial block at pixel index l as a vector for each direction and concatenates vectors from all directions into a matrix as described above in relation to FIG. 1, and $\Omega$ is the set of all non-overlapping blocks that uniformly tile the image domain. The nuclear norm $\|\cdot\|_*$, which is the convex envelope of the rank constraint and which is equivalent to the sum of the matrix's eigenvalues, is used to reduce the computational complexity.

The above model is bilinear in terms of magnitude and phase, and we use alternating minimization with respect to the magnitude and phase separately to solve the reconstruction problem. The phase of each shot and each direction can be updated individually. In terms of phase $\theta_{d,s}$, the subproblem is $$\min_{\theta_{d,s}} \frac{1}{2} \|E_{d,s} FS(m_d \cdot \exp(j\theta_{d,s})) - y_{d,s}\|_2^2. \quad (5)$$

Let $$A_{d,s} = E_{d,s} FS \quad (6)$$

and $$r_{d,s} = A_{d,s}^T [A_{d,s}(m_d \cdot \exp(j\theta_{d,s})) - y_{d,s}]. \quad (7)$$

The gradient $gp_{d,s}$ with respect to $\theta_{d,s}$ can be derived as follows, $$gp_{d,s} = \text{Real}(j \exp(-j\theta_{d,s}) \cdot m_d \cdot r_{d,s}), \quad (8)$$

where Real(x) takes the real part of x. We use this to apply a gradient descent step, and the update rule for $\theta_{d,s}$ in the k-th iteration is $$\theta_{d,s}^{k+1} = \theta_{d,s}^k + agp_{d,s}^k,$$

where a is the step size.

Unlike phase images, magnitude images from all directions have to be updated simultaneously because of the use of the LLR regularization term. We use the proximal gradient method to update the magnitude images. The subproblem in terms of magnitude m is $$\min_m \Sigma_d \Sigma_s \frac{1}{2} \|E_{d,s} FS(m_d \cdot \exp(j\theta_{d,s})) - y_{d,s}\|_2^2 + \lambda_1 \Sigma_{l \in \Omega} \|R_l m\|_*. \quad (10)$$

Similarly, the gradient of the first term with respect to $m_d$ is $$gm_d = \text{Real}(\exp(\Sigma_s \exp(-j\theta_{d,s}) \cdot r_{d,s}). \quad (11)$$

where, as usual, the sum is over values of s ranging from 1 to NS.

Defining $gm = [gm_1, \ldots, gm_{ND}]^T$, the update rule for m in the k-th iteration is $$m^{k+0.5} = m^k + agm^k / NS, \quad (12)$$

$$m^{k+1} = P_{\lambda_1 g_m}(m^{k+0.5}), \quad (13)$$

where $P_{\lambda_1 g_m}$ is the proximal operator of $\lambda_1 g_m$. In this case, $g_m(m)$ is the LLR regularization term, which is the summation of nuclear norms of all spatial-angular matrices. Based on the definition of the proximal operator, Eq. 13 could be written as follows, $$m^{k+1} = \arg\min_m \frac{1}{2} \|m - m^{k+0.5}\|_2^2 + \lambda_1 \Sigma_{l \in \Omega} \|R_l m\|_*, \quad (14)$$

By using non-overlapped blocks, this problem can be separated into many sub-problems, and an analytical solution exists. Each matrix can be updated separately by applying soft-thresholding to its eigenvalues. In each iteration, random shifts along frequency encoding and phase encoding directions are added when constructing those blocks to achieve shift invariance.

Figure 2:
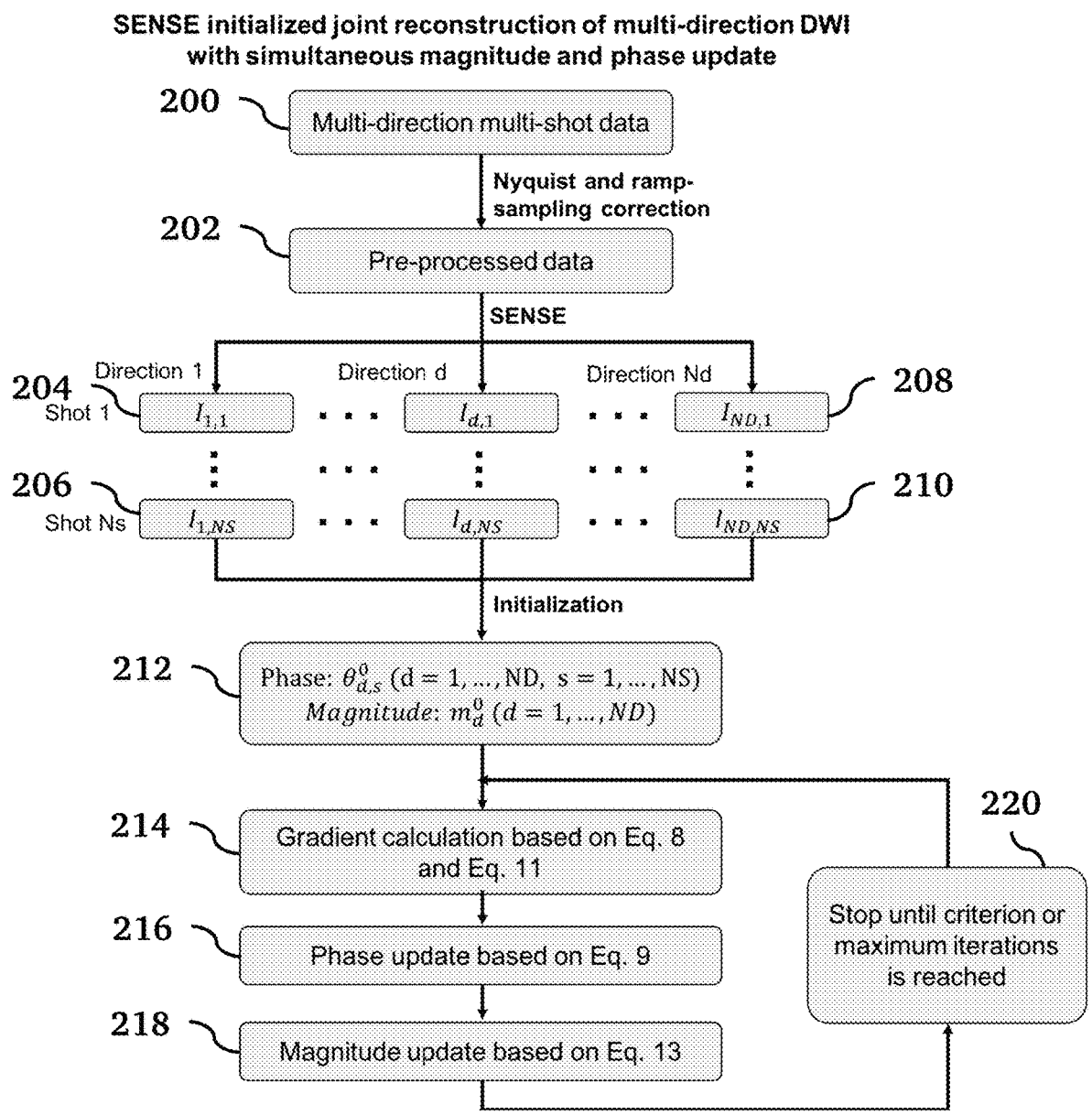
FIG. 2 is a flowchart illustrating a DW image reconstruction pipeline, according to an embodiment of the invention.

In summary, the phase and magnitude images are updated based on Eq. 9 and Eq. 13 separately in each iteration, until convergence or a maximum number of iterations is reached. The reconstruction processing pipeline is shown in FIG. 2, FIG. 2. In step 200 the raw multi-direction, multi-shot MRI data is acquired by an MRI scanner. In step 202 the acquired data is pre-processed by the product algorithm for Nyquist-ghost and ramp-sampling correction. SENSE reconstruction results for each individual shot and direction are used as initialization of the non-linear model. For example, the figure shows initialized images for first and last shots 204 and 206 of direction 1 and first and last shots 208 and 210 of direction ND. In step 212 the initialized complex images are decomposed into phase and magnitude components. The method then iterates steps 214, 216, 218, 220. In each iteration, phase and magnitude images are updated separately. Specifically, in step 214 a gradient calculation is performed based on Eq. 8 and Eq. 11. In step 216 the phase images are updated based on Eq. 9, and in step 218 the magnitude images are updated based on Eq. 13. Step 220 stops the iteration if a criterion or maximum number of iterations has been reached. The phase and magnitude images at the completion of the iteration are then combined to form final reconstructed complex images.

The pseudo-algorithm for the reconstruction is shown below in Table 1.

TABLE 1

Pseudo-algorithm to solve the proposed model.
Pseudo-algorithm

Input: k-space data y, encoding operator A, magnitude and phase initialization $m^0$ and $\theta^0$, regularization parameter $\lambda$
Output: final magnitude images m and phase images $\theta$
1: Repeat:
2:     Calculate the gradient of phase image of each shot and direction (Eq.7 and Eq.8)
3:     Update phase images and get $\theta^{k+1}$ (Eq.9)
4:     Calculate the gradient of magnitude image of each direction (Eq.7 and Eq.11)
5:     Update magnitude images and get $m^{k+0.5}$ (Eq.12)
6:     Construct spatial-angular matrices (Fig. 1), perform SVD, apply soft-thresholding to their singular values and get updated magnitude images $m^{k+1}$ based on the new singular values (Eq.14)
7: Until stopping criterion is reached Several experiments were performed to test and validate the methods of the present invention. In these experiments, data were acquired from seven healthy volunteers on a 3 T GE Signa Premier scanner using a 48-channel head receive-only coil. Six experiments were performed for different purposes. For all scans, a 2D single-refocused Stejskal-Tanner diffusion-weighted spin-echo EPI sequence was used to acquire about 10 axial slices covering the corpus callosum, with left-right readout direction, +/−250 kHz bandwidth, four shots (except for Experiments 0 and 4), a b-value of 1,000 s/mm² (except for Experiments 0 and 5), and one interleaved non-diffusion-weighted image (b=0) for every 14 DW images for image co-registration. The scan parameters of all experiments are summarized in FIG. 11.

Experiment 0 acquired high SNR data to validate the feasibility of the proposed method and investigate the influence of the regularization parameter X on the reconstruction results. Experiment 1 was performed to select reconstruction parameters. Data were acquired along only 30 directions to enable fast reconstruction. Experiment 2 included two consecutive scans to compare the performance of single-shot and multi-shot scans with the same resolution and number of diffusion-encoding directions. Four repetitions were acquired in the single-shot scan to match the acquisition time of the 4-shot scan. Experiment 3 was designed to test the performance of the proposed method on data with different resolutions (0.9 mm, 0.8 mm and 0.7 mm isotropic). The data were acquired along 75 diffusion-encoding directions such that the total scan time was within one hour. Experiment 4 only included a 4-shot scan with 0.9 mm isotropic resolution and 150 directions to further improve the angular resolution compared with Experiment 3. Experiment 5 was designed to validate the proposed method on data acquired with a higher b-value.

For comparison, the multi-shot data were reconstructed by the online GE MUSE reconstruction and by using the methods of the present invention as discussed above in relation to FIG. 2. The acquired raw k-space data were first pre-processed in step 202 for Nyquist-ghost correction and ramp-sampling correction using the product algorithm provided by GE's Orchestra software. The multi-shot non-diffusion-weighted k-space data were simply combined together since there were no phase variations in the absence of diffusion-encoding gradients. Sensitivity maps were calculated from the non-diffusion-weighted images using ESPIRiT. SENSE reconstruction was performed on DW data of each individual shot and direction using BART. Low-resolution phase images after Hanning windowing and averaged magnitude images of the SENSE results were used as the initialization of data for the iterative algorithm. The reconstruction settings were selected based on the reconstruction results of Experiment 1 and are summarized in Table 2. The same settings were used for all experiments. A small range of the regularization parameter was suggested based on Experiment 1. The step size a was chosen as 0.9, and 100 iterations (chosen empirically) achieved good convergence. The block size of the LLR term was chosen as eight following previous LLR methods. The absolute value of reconstructed magnitude images was used for the diffusion model fitting. For the product MUSE reconstruction, sensitivity maps were calculated from an extra calibration scan, and homodyne was used after MUSE reconstruction for partial Fourier reconstruction.

TABLE 2

| Parameters | Values |
| --- | --- |
| Number of iterations | 100 |
| Initialization of phase | hanning window (width = ½ matrix size) |
| Step size for phase and magnitude update | 0.9 |
| Regularization parameter for LLR | 0.12~0.18 |
| Block size | 8 |
| Phase update (Yes/No) | Yes |

Summary of Selected Reconstruction Parameters

DWI data were corrected for eddy current distortions and bulk motion, and co-registered using the eddy function from the FMRIB Software Library (FSL, http://fsl.fmrib.ox-.ac.uk/fsl/fslwiki/). The diffusion tensor model was then fitted using FSL's dtifit function to derive the fractional anisotropy (FA) and the primary eigenvector (V1). The "ball-and-stick" model (3 sticks) was fitted using FSL's "bedpostx" function on the b=0 and 2,000 s/mm$^2$ data to derive the primary, secondary, and tertiary fiber orientations (dyads1, dyads2, and dyads3, respectively) and their associated volume fractions (f1, f2, and f3, respectively).

Figure 3:
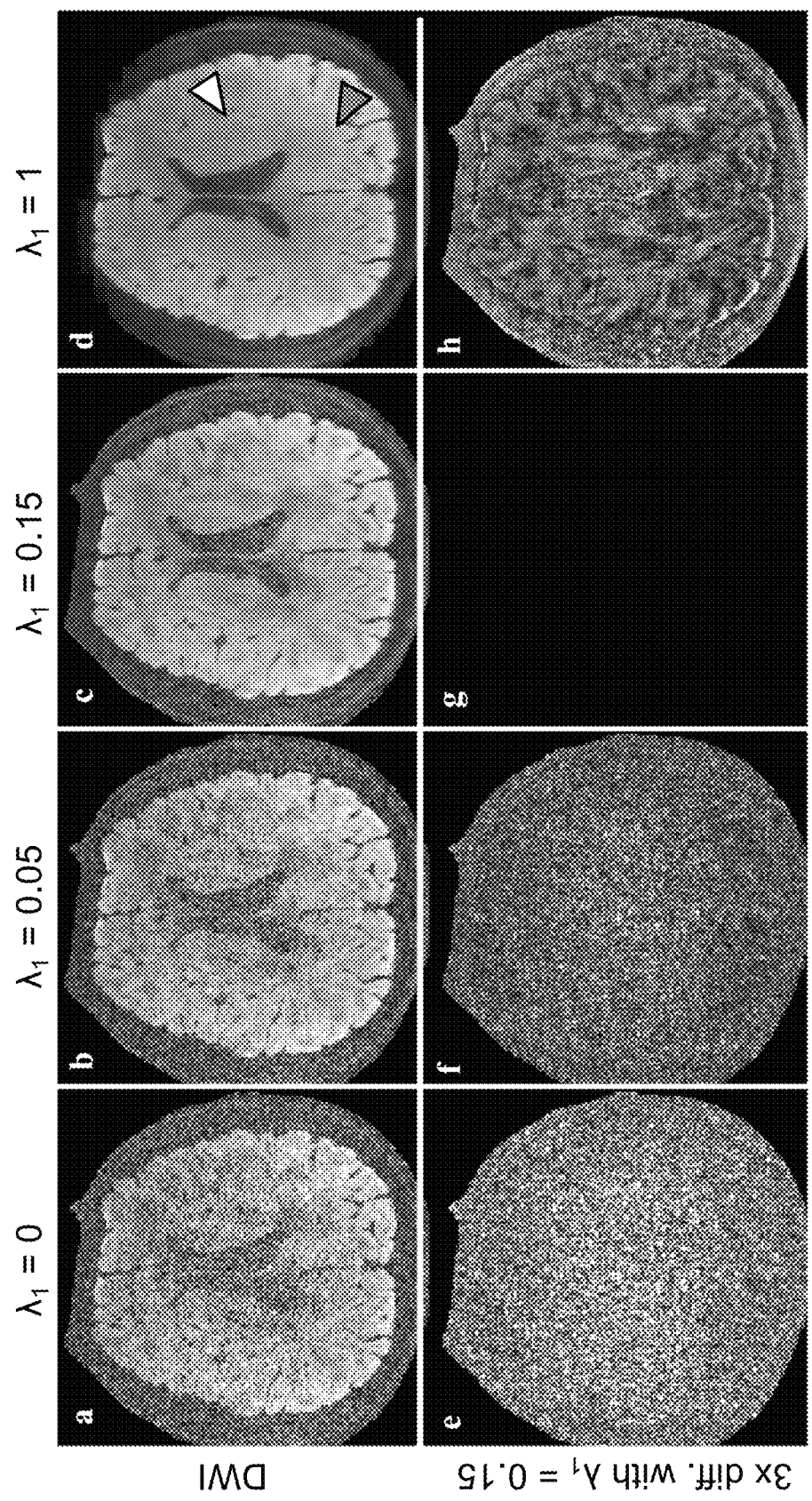
FIG. 3 shows DW images reconstructed with different regularization parameters, according to an embodiment of the invention.

FIG. 3 shows in the top row a collection of DW images reconstructed using different values of the regularization parameter $\lambda_1$ (Eq. 4) and in the bottom row the corresponding 3 times difference images relative to the image reconstructed with $\lambda_1$=0.15.

Figure 9:
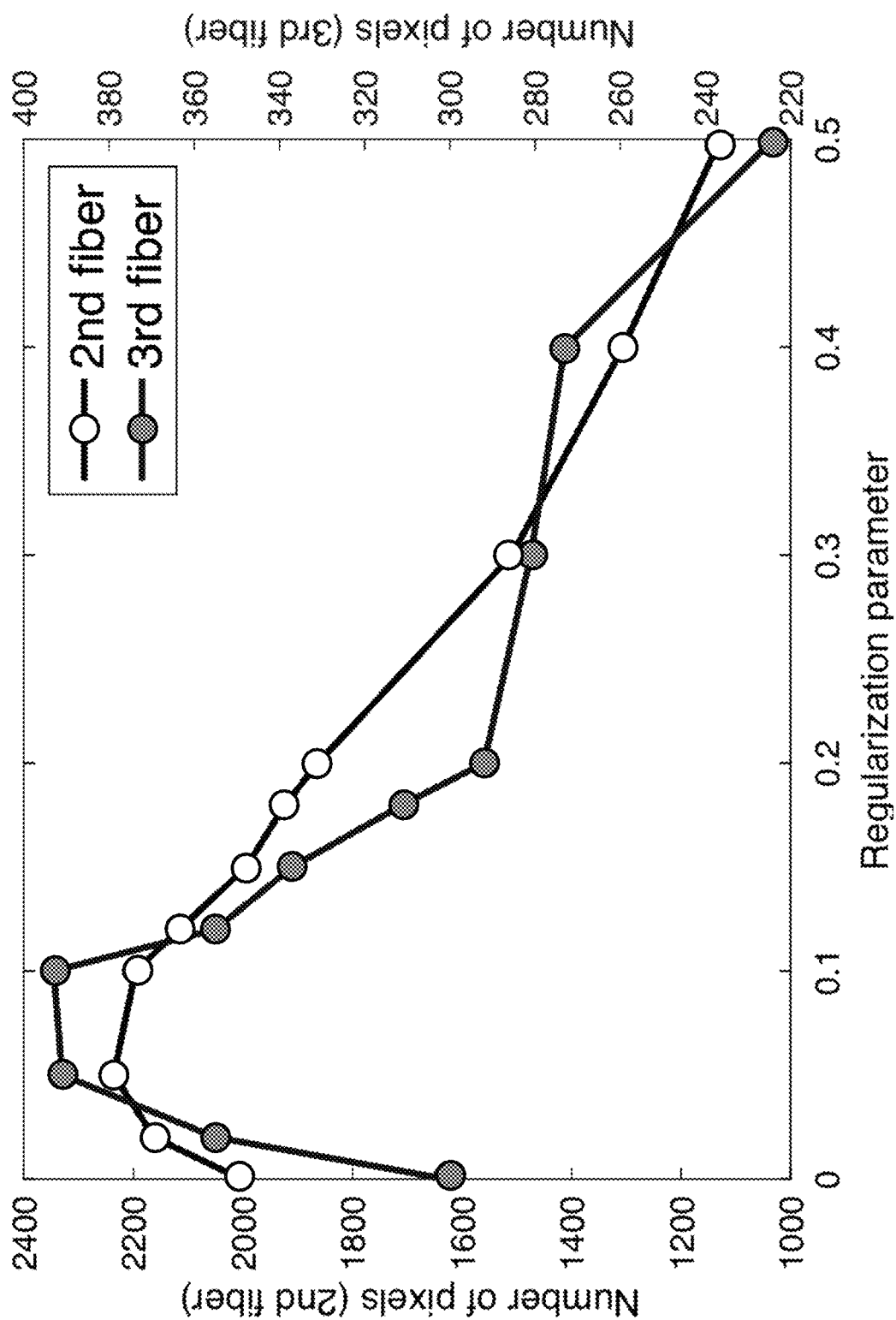
FIG. 9 is a graph of the total number of pixels versus regularization parameter comparing second and third fibers, according to an embodiment of the invention.

As shown in the first column ($\lambda_1$=0), when no angular correlation is used and each direction is reconstructed individually, the result is very noisy. As shown in the second and third columns ($\lambda_1$=0.05 and $\lambda_1$=0.15), as $\lambda_1$ increases, the noise level decreases. As shown in the fourth column ($\lambda_1$=1), when $\lambda_1$ is too large, some structures are lost and blocky artifacts show up, e.g., at locations indicated by the two triangle pointers. Because the noise level of the data can also influence the choice of this regularization parameter, we provide a range of $\lambda_1$ in Table 2. We use $\lambda$=0.12 for 1.2 mm isotropic data and $\lambda$=0.15 for 0.9 mm isotropic data. Supporting Information FIG. 9 shows how this parameter would influence the estimated number of crossing fibers, which highly depends on the angular anisotropy.

Figure 4:
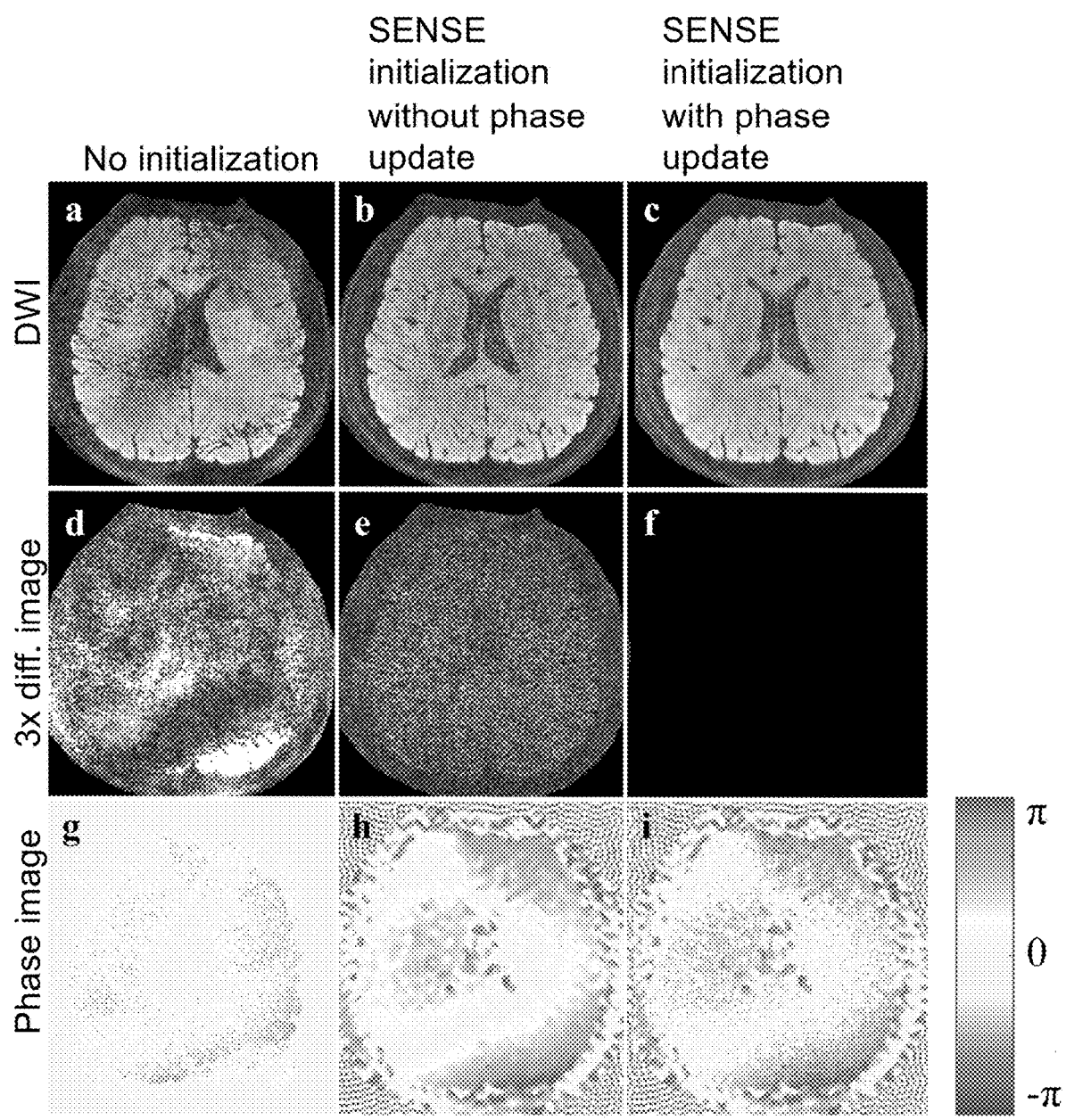
FIG. 4 shows reconstructed DW images with different reconstruction settings, according to an embodiment of the invention.

FIG. 4 shows in the top row DW images reconstructed with no initialization, SENSE initialization, and SENSE initialization with phase updates, in the second row their corresponding three times difference images, and in the third row the phase images of the first shot. As shown in the first column, where no image initialization is used, the reconstructed DWI image has artifacts due to the difficulty of non-linear optimization. As illustrated in the second column, using SENSE as initialization eliminates many of the artifacts. As illustrated in the third column, using SENSE initialization with phase updates during reconstruction further refines the results by recovering high-frequency phase information and to further decrease noise levels in the magnitude image.

Figure 5:
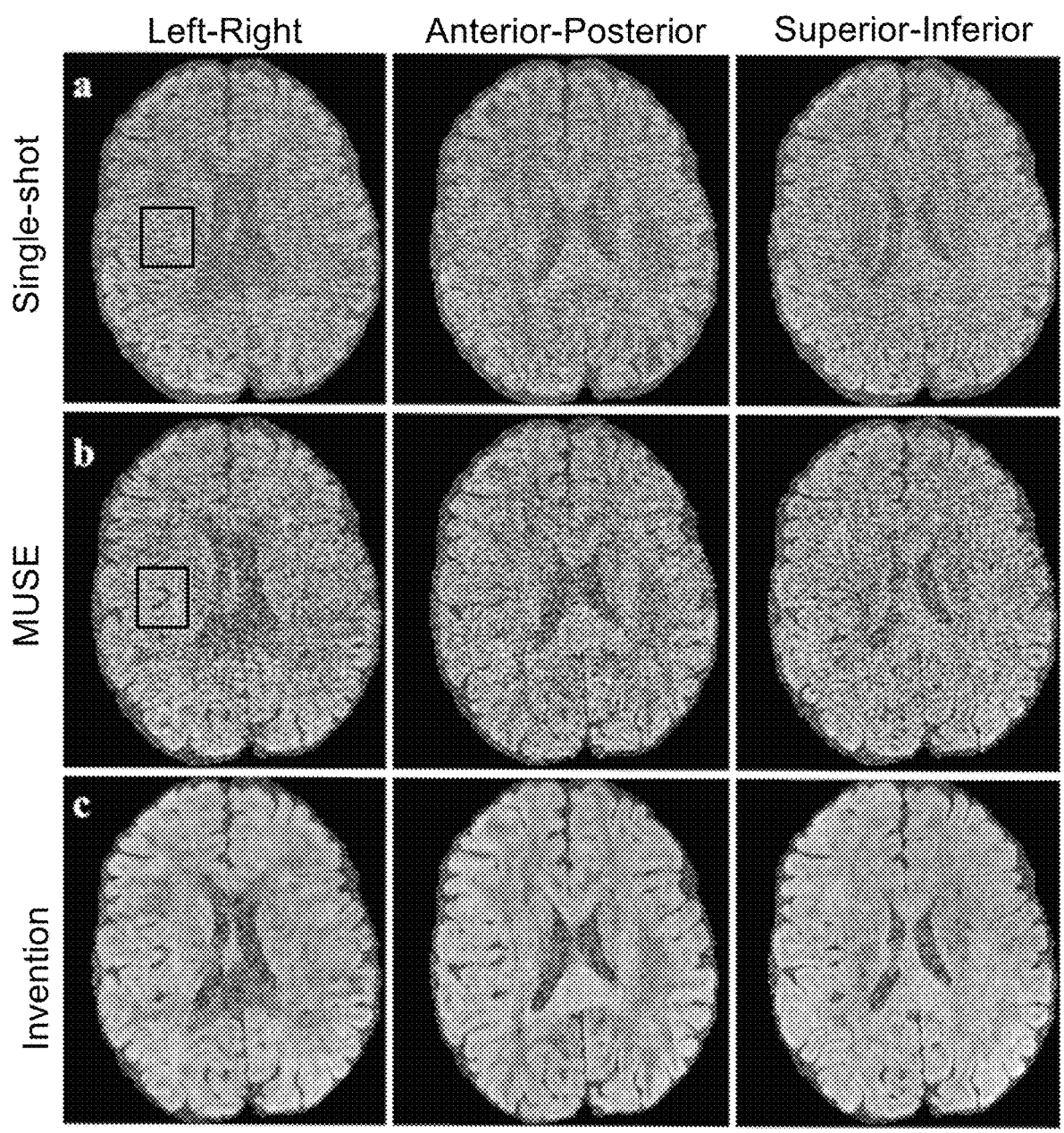
FIG. 5 shows reconstructed DW images along different diffusion-encoding directions for single-shot, multi-shot MUSE, and multi-shot using techniques of the invention.

FIG. 5 shows reconstructed DW images along left-right (left column), anterior-posterior (middle column), superior-inferior (right column) diffusion-encoding directions, reconstructed using single-shot imaging (top row), multi-shot imaging with MUSE (middle row), and multi-shot imaging with the present method (bottom row). The multi-shot MUSE reconstruction shows decreased noise level compared to single-shot imaging with multiple repetitions. Some structure is lost due to the high noise level in single-shot imaging as indicated by the boxed region. The noise levels are significantly reduced by the methods of the invention, which demonstrates its ability to utilize the correlation between different diffusion-encoding directions. The distortion level due to off-resonance in multi-shot images is reduced by a factor of 1.3 compared with that of single-shot images with a parallel imaging factor of 3, which is consistent with the effective echo spacing as shown in Table 2. However, the distortion levels are visually similar since the brain regions covered by the displayed axial slices contain minimal susceptibility variations.

Figure 6:
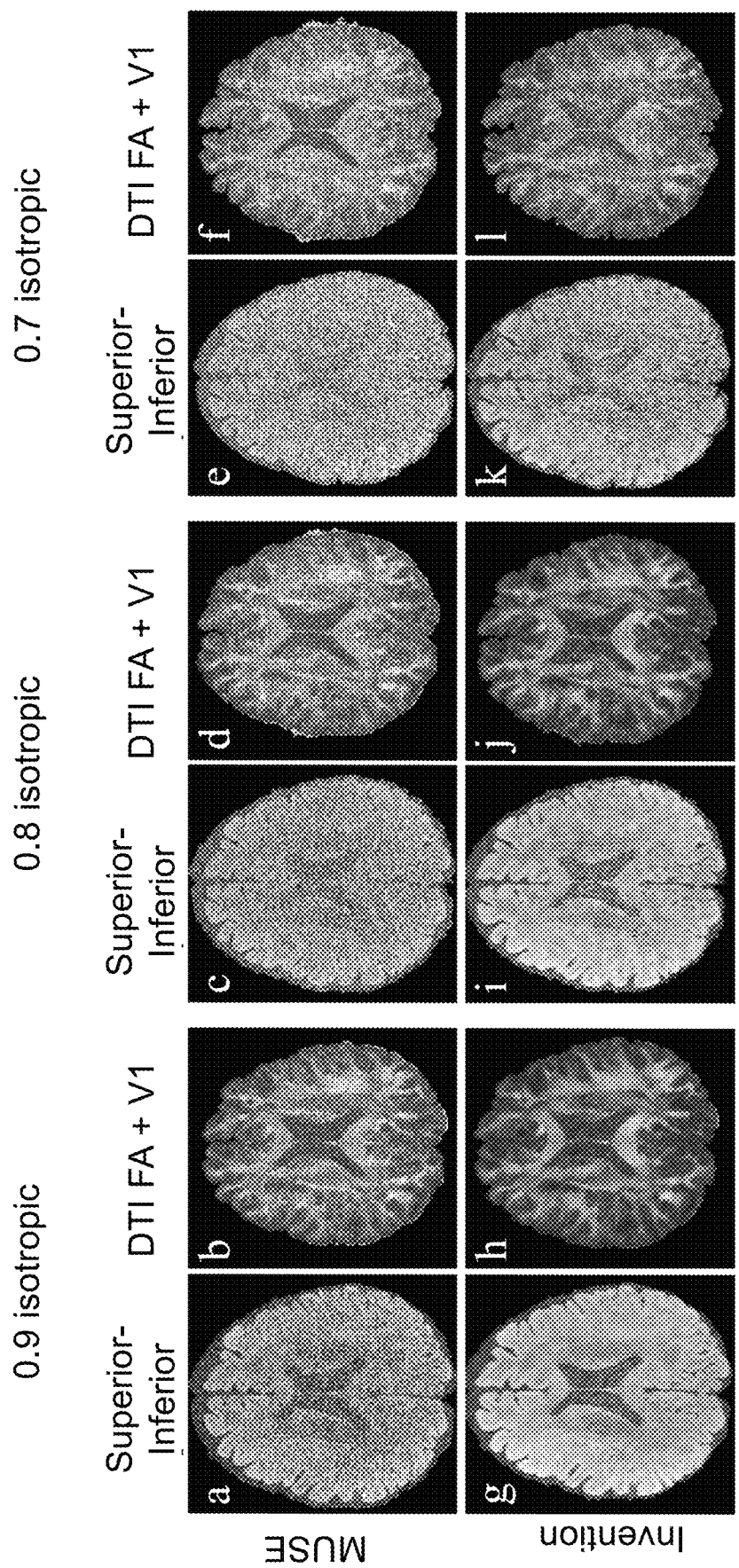
FIG. 6 shows reconstructed DW images along different diffusion-encoding directions for different isotropic resolution, comparing MUSE with techniques of the invention.

The improvement provided by the methods of the present invention compared with MUSE is more significant at a higher resolution. FIG. 6 shows reconstructed DW images for three different isotropic resolutions (shown in different columns) comparing MUSE with the method of the present invention (shown in the two rows). Also shown are corresponding color-encoded V1 maps weighted by FA. These results are representative axial slice images from Experiment 3 (0.9 mm, 0.8 mm and 0.7 mm isotropic resolution, 1,000 s/mm$^2$ b-value). The windows of V1 maps are tuned separately for better visual quality (0-1 for MUSE, and 0-0.8 for the proposed method). The DW images reconstructed by MUSE (top row) are very noisy, resulting in noisy FA maps and erroneous V1 vectors. The DW images reconstructed by the present method (bottom row) show markedly reduced noise levels in comparison.

Figure 7:
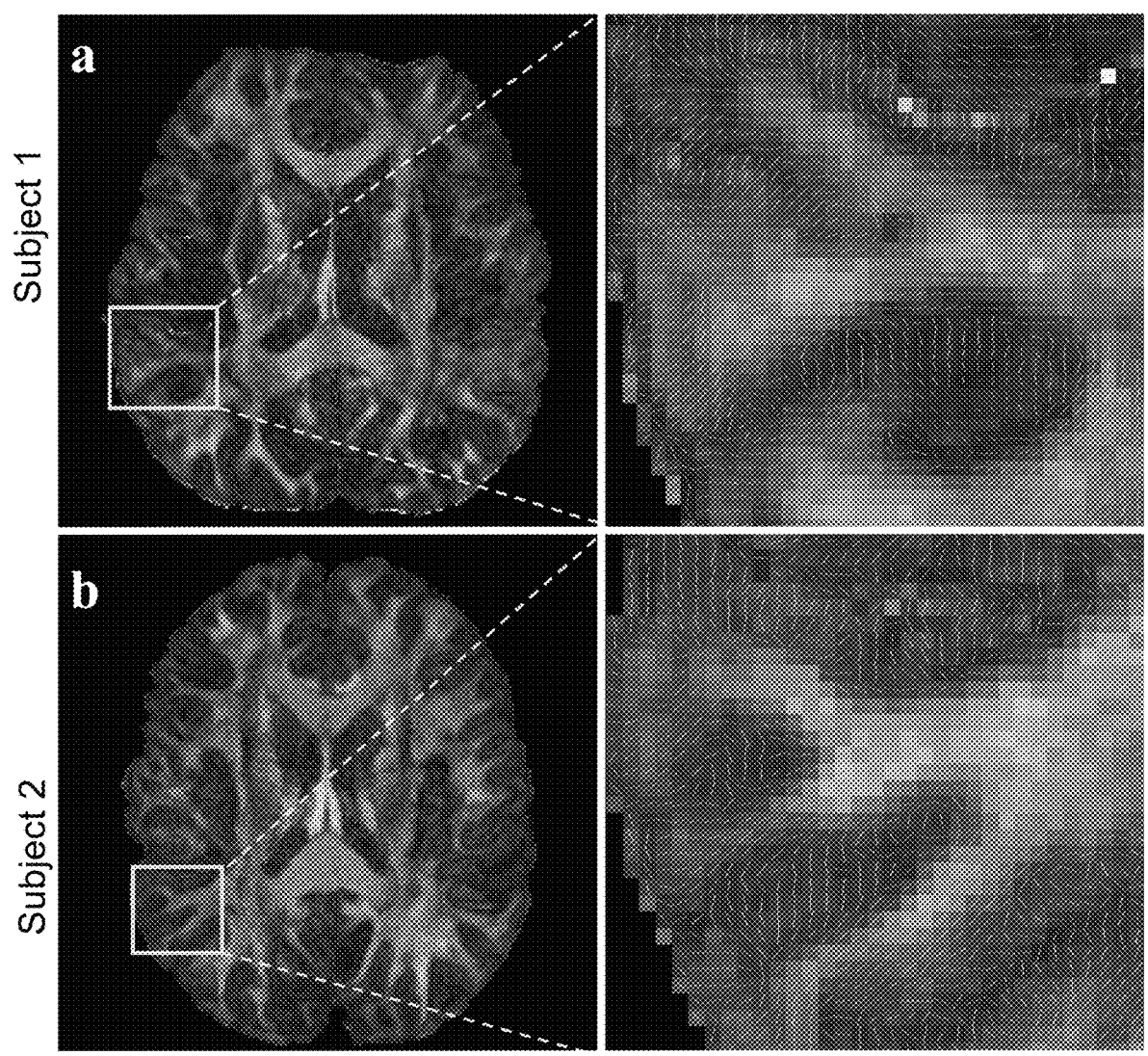
FIG. 7 shows V1 maps weighted by FA for two subjects, according to an embodiment of the invention.

FIG. 7 displays direction-encoded FA maps with 0.9 mm isotropic resolution and 150 diffusion-encoding directions reconstructed by the present method from two subjects (top row and bottom row). The primary eigenvector V1 in the cortex can be clearly visualized, which is dominantly radial to the cortical surface. In addition, we selected and reconstructed 15, 30, 45, 60, and 75 out of 150 directions using the present method and MUSE. The window level is tuned separately for better visual quality (0-0.8 for subject 1, and 0-1 for subject 2). The zoomed-in view in the second column shows the primary eigenvector V1 in the cortex.

Figure 10:
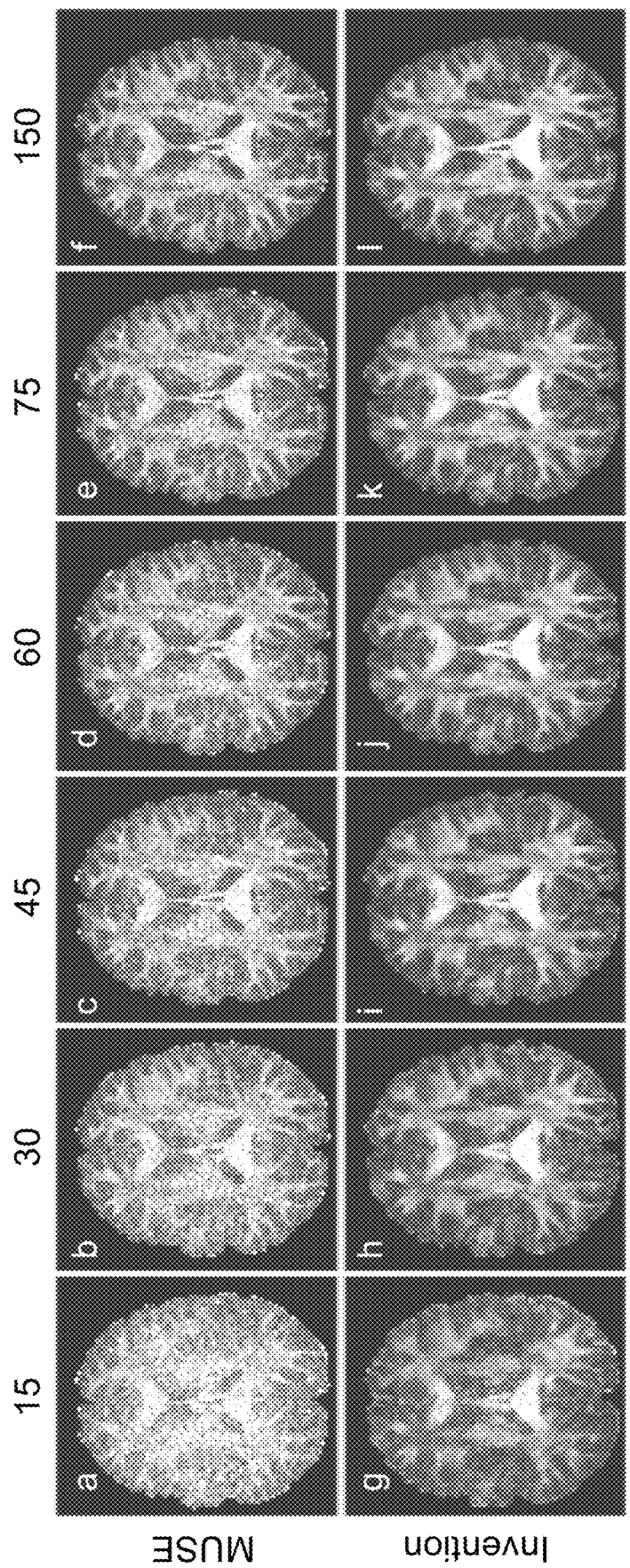
FIG. 10 shows estimated FA maps from reconstruction results of various directions, comparing MUSE with techniques of the invention.

FIG. 10 shows estimated FA maps from reconstruction results of 15, 30, 45, 60 and 75 directions selected from 150 directions by MUSE (first row) and the present method (second row) from Experiment 4 (0.9 mm isotropic resolution, 1,000 s/mm$^2$ b-value). For different numbers of selected directions (different columns), the present method shows significantly decreased noise levels compared with MUSE by inspection. With an increased number of diffusion-encoding directions, the noise level in FA maps decreases for both the present method and MUSE. Starting from 60 directions, no noticeable difference could be visualized in the present method when comparing with the FA map from 150 directions.

Figure 8:
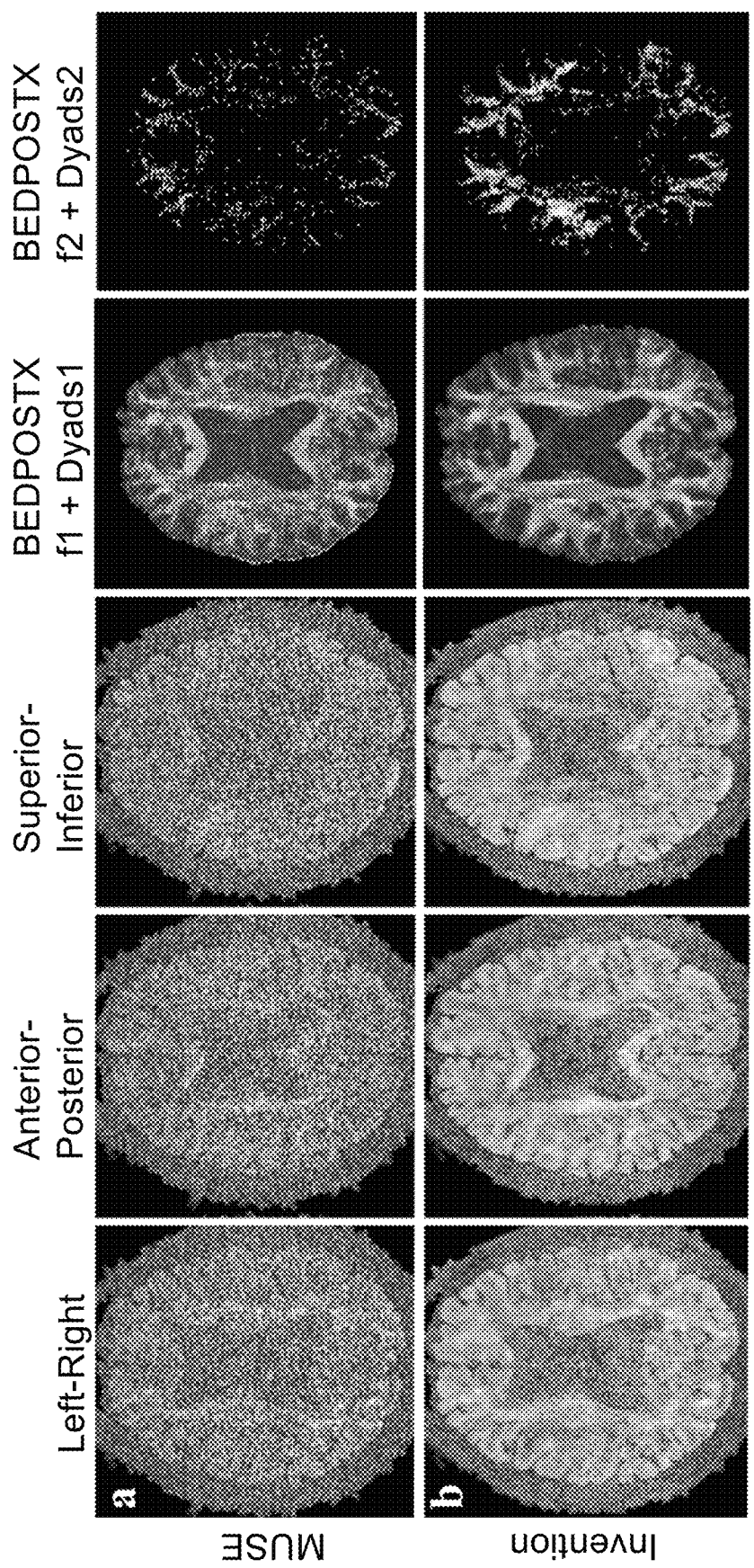
FIG. 8 shows 4-shot high b-value DW images for three different directions, corresponding f1-encoded Dyads1 maps, and f2-encoded Dyads2 maps, comparing MUSE with techniques of the invention.

FIG. 8 shows in the first three columns 4-shot high b-value DW reconstructed images for three out of 75 directions, corresponding f1-encoded Dyads1 maps (fourth column) and f2-encoded Dyads2 maps (fifth column), where the first row shows images reconstructed by MUSE and the second row shows images reconstructed using the present method. These images are from Experiment 5 (1 mm isotropic resolution, 2,000 s/mm$^2$ b-value). A threshold of 0.05 was used for both results. The present method shows improvements for high b-value images. As shown in the fifth column, the present method estimates more voxels with a second fiber compared with MUSE.

As the experimental results demonstrate, the present method, with simultaneous phase and magnitude updates, solves the phase variation problem in DWI reconstruction. The separate estimation of phase and magnitude images allows constraints to be directly applied to the magnitude images. We use LLR on the magnitude images from all diffusion-encoding directions to utilize their angular correlation. The non-linear model and spatial-angular LLR regularization together remove phase variations between both shots and directions and substantially reduce noise levels in DW images.

The method allows additional regularization terms such as a Gaussian prior or total variation to be incorporated. The separation of magnitude and phase estimation and the low-resolution phase initialization inherently provide partial Fourier reconstruction. In addition, the method may include additional constraints on the phase images, although this would increase the complexity of the algorithm, which needs to account for phase wraps. The current reconstruction of one slice with size 224×224, 48 channels and 150 directions takes approximately 3 hours on a Linux workstation with a 2.3 GHz CPU and a 256 GB RAM.

In the present method, the specific value of the regularization parameter for LLR is determined by techniques as discussed above in relation to FIG. 3. Other reconstruction settings such as block size are consistent for different datasets and are determined based on Experiment 1. We notice that when the regularization parameter is large, the reconstructed DW images can still look clean without blocky artifacts, while the FA maps become blurry with reduced values. This is because a very large regularization term may eliminate the real variations of the diffusion signals along different directions.

A trade-off between the denoising level and angular smoothing is shown in FIG. 9, which graphs the total number of pixels with the second fiber and the third fiber versus different regularization parameters for reconstruction. A threshold of 0.05 was used for counting. This data uses "bedpostx" results from Experiment 0 (2 mm isotropic resolution, 2,000 s/mm$^2$ b-value). The joint reconstruction with a suitable regularization parameter (about 0.1 in this case) enables more crossing fibers to be detected, while further increasing the regularization parameter oversmooths the images such that fewer crossing fibers can be detected. Increasing the number of diffusion-encoding directions or decreasing spatial resolution helps to avoid this problem because a smaller regularization parameter can be used in these cases. The choice of the optimal regularization parameter depends on spatial resolution, b-value, block size, and the number of diffusion-encoding directions. We performed a grid search in Experiment 1 to empirically select a small range for this parameter. We fine-tuned this parameter by a small amount within this range when applied to data acquired with different parameters, and this strategy worked well. Auto-selection of the regularization parameters using more advanced methods may also be used.

We note that a proper initialization, especially for the phase images, is preferred since the proposed model is non-convex. In these examples, we used SENSE reconstruction as initialization works well, but other initialization methods and optimization methods may also be used. Further refining the phase estimation in each iteration also helps with the estimation of magnitude images, because the initial phase estimation from the SENSE reconstruction is not sufficiently accurate. The block size of LLR is set as 8, and it does not make much difference to change it to 6 or 10.

Multi-shot imaging can achieve better image quality compared with single-shot imaging within the same scan time. This improvement may be because of 1) the reduction of TE (64 ms for single-shot and 51 ms for 4-shot as in FIG. 11), and 2) the fact that multi-shot reconstruction utilizes the shot-to-shot correlation to obtain the DW images of each direction, while using only magnitude averaging to combine different repetitions of single-shot images can increase noise levels. Because the online GE MUSE reconstruction works robustly with no ghosting artifacts and is readily available, we use it as a reference for comparison. Significantly reduced noise levels could be visualized when comparing our proposed method with the product MUSE reconstruction. Notably, our reconstruction method and the product MUSE reconstruction utilize different sensitivity maps (computed based on the b=0 image and from an external reference scan, respectively) and homodyne is used after product MUSE for partial Fourier reconstruction. Those differences might introduce some confounding factors especially for quantitative comparisons.

One disadvantage of multi-shot imaging is the increased scan time. Some advanced acquisition strategies like simultaneous multi-slice imaging or reduced-FOV excitation could be combined with multi-shot imaging to help accelerate the acquisition. The present method can also be applied to other sampling patterns with a minor modification of the data consistency term in Eq. 4.

$$\min_m \Sigma_d \Sigma_s \tfrac{1}{2} \|E_{d,s} FS(m_d \cdot \exp(j\theta_{d,s})) - y_{d,s}\|_2^2 + \lambda_1 \Sigma_{l \in \Omega} \|R_l m\|_*. \tag{10}$$

This modification could be achieved by changing the sampling pattern (E in Eq. 4) accordingly, or using non-uniform Fourier transform instead of Fourier transform (F in Eq. 4).

The present method takes phase variations into account, while the inter-volume rigid motion (displacement) is corrected in the post-processing step. The image translation due to the rigid motion and the mismatched image distortion due to eddy currents between different diffusion-encoding directions may decrease the angular correlation. For scan times as long as 30 minutes and b-values as high as 2,000 s/m², the proposed method still shows remarkable improvements. A linear or non-linear transform could also be included in the data consistency term to correct this mismatch between directions.

In conclusion, the present multi-shot DWI reconstruction technique with simultaneous phase and magnitude updates enables regularization on magnitude images. Spatial-angular matrices are constructed from magnitude images of all diffusion-encoding directions. Low-rank regularization is applied to these matrices to exploit the angular correlation. Experiments demonstrate that the joint reconstruction method substantially improves the quality of high-resolution and high b-value DWI.

The invention claimed is:

1. A method for diffusion-weighted magnetic resonance imaging (MRI), the method comprising:
   a) performing by an MRI scanner a multi-direction, multi-shot, diffusion-weighted MRI scan to produce MRI scan data;
   b) jointly reconstructing from the MRI scan data
      1) magnitude images for multiple diffusion-encoding directions and
      2) phase images for multiple shots and multiple diffusion-encoding directions using an iterative reconstruction method;
   wherein each iteration of the iterative reconstruction method comprises a gradient calculation, a phase update to update the phase images, and a magnitude update to update the magnitude images;
   wherein each iteration minimizes a cost function comprising a locally low-rank (LLR) regularization constraint on the magnitude images from the multiple diffusion-encoding directions.

2. The method of claim 1 further comprising decomposing images of the MRI scan data into magnitude images and phase images.

3. The method of claim 1 wherein the locally low-rank (LLR) regularization constraint on the magnitude images from the multiple diffusion-encoding directions includes a sum over local spatial image blocks.

4. The method of claim 1 wherein the locally low-rank (LLR) regularization constraint includes operators for local spatial image blocks, formed by concatenating vectors containing magnitude image data from multiple diffusion-encoding directions.

5. The method of claim 1 wherein the cost function comprises a data consistency term that sums over all diffusion-encoding directions and sums over all shots.

* * * * *